(12) United States Patent
Force

(10) Patent No.: US 10,022,399 B1
(45) Date of Patent: Jul. 17, 2018

(54) NUTRITIONAL COMPOSITION FOR PROVIDING RELIEF FROM WINE INDUCED HEADACHES

(71) Applicant: Mark Campbell Force, Ashland, OR (US)

(72) Inventor: Mark Campbell Force, Ashland, OR (US)

( * ) Notice: Subject to any disclaimer, the term of this patent is extended or adjusted under 35 U.S.C. 154(b) by 0 days.

(21) Appl. No.: 15/078,982

(22) Filed: Mar. 23, 2016

Related U.S. Application Data

(60) Provisional application No. 62/160,538, filed on May 12, 2015.

(51) Int. Cl.
| | |
|---|---|
| A61K 33/24 | (2006.01) |
| A61K 31/455 | (2006.01) |
| A61K 31/355 | (2006.01) |
| A61K 36/31 | (2006.01) |
| A61K 33/04 | (2006.01) |
| A61K 31/51 | (2006.01) |
| A61K 31/525 | (2006.01) |
| A61K 31/4415 | (2006.01) |
| A61K 31/519 | (2006.01) |
| A61K 31/353 | (2006.01) |
| A61K 36/899 | (2006.01) |
| A61K 36/48 | (2006.01) |
| A61K 36/21 | (2006.01) |
| A61K 36/23 | (2006.01) |
| A61K 36/534 | (2006.01) |
| A61K 9/48 | (2006.01) |
| A23L 1/29 | (2006.01) |
| A23L 1/302 | (2006.01) |
| A23L 1/304 | (2006.01) |
| A23L 1/305 | (2006.01) |
| A23L 1/30 | (2006.01) |

(52) U.S. Cl.
CPC .............. *A61K 33/24* (2013.01); *A23L 1/296* (2013.01); *A23L 1/3002* (2013.01); *A23L 1/302* (2013.01); *A23L 1/304* (2013.01); *A23L 1/3051* (2013.01); *A61K 9/48* (2013.01); *A61K 31/353* (2013.01); *A61K 31/355* (2013.01); *A61K 31/4415* (2013.01); *A61K 31/455* (2013.01); *A61K 31/51* (2013.01); *A61K 31/519* (2013.01); *A61K 31/525* (2013.01); *A61K 33/04* (2013.01); *A61K 36/21* (2013.01); *A61K 36/23* (2013.01); *A61K 36/31* (2013.01); *A61K 36/48* (2013.01); *A61K 36/534* (2013.01); *A61K 36/899* (2013.01); *A23V 2002/00* (2013.01)

(58) Field of Classification Search
CPC .......... A61K 33/24; A61K 9/48; A61K 36/48; A61K 36/534; A61K 36/23; A61K 36/21; A61K 36/31; A61K 36/899; A61K 31/355; A61K 31/353; A61K 31/519; A61K 31/4415; A61K 31/455; A61K 31/525; A61K 31/51; A61K 33/04; A23L 1/296; A23L 1/3051; A23L 1/304; A23L 1/302; A23L 1/3002; A23V 2002/00
See application file for complete search history.

(56) References Cited

U.S. PATENT DOCUMENTS

| | | | |
|---|---|---|---|
| 5,712,309 A | 1/1998 | Finnin et al. | |
| 6,245,360 B1 * | 6/2001 | Markowitz | ............ A23L 33/16 424/464 |
| 6,485,758 B2 | 11/2002 | Mirza et al. | |
| 6,913,769 B2 | 1/2005 | Oslick et al. | |
| 6,967,031 B1 | 11/2005 | Oslick et al. | |
| 8,298,597 B2 | 10/2012 | Muller | |
| 8,377,907 B1 | 2/2013 | Halamicek | |
| 8,507,015 B2 | 8/2013 | Thorsby et al. | |
| 2002/0006910 A1 | 1/2002 | Miasnikov et al. | |
| 2007/0202215 A1 | 8/2007 | Lak | |
| 2015/0004282 A1 * | 1/2015 | Mills | ......................... A23L 2/38 426/72 |
| 2017/0173097 A1 * | 6/2017 | Horn | ...................... A61K 36/31 |

FOREIGN PATENT DOCUMENTS

JP      406014746 A   *   1/1994

* cited by examiner

*Primary Examiner* — Snigdha Maewall
(74) *Attorney, Agent, or Firm* — Jerry Haynes Law

(57) ABSTRACT

A dietary nutritional supplement that provides relief for light to moderate wine consumers who experience headaches triggered by light to moderate wine consumption. The nutritional composition consists of at least one member selected from the group of ingredients consisting of: Molybdenum, Selenium, Vitamin B1, Vitamin B2, Vitamin B3, Vitamin B6, Folic acid, Quercetin, and Vitamin E. Alternative embodiments may include nitrogreens. The ingredients for the composition form a synergy with each other to improve metabolism of wine constituents. A method of use requires six sequential weeks of administering the composition in pill form and in predetermined quantities with predetermined amounts of wine. A survey questionnaire is given to experimental subjects to help assess the efficacy of the nutritional composition.

3 Claims, 3 Drawing Sheets

100

| | Ingredient | Range of Quantity |
|---|---|---|
| 102 | Molybdenum | about 10 mcg to about 600 mcg |
| 104 | Selenium | about 10 mcg to about 600 mcg |
| 106 | Vitamin B1 | about 0.1 mg to about 2000 mg |
| 108 | Vitamin B2 | about 0.1 mg to about 2000 mg |
| 110 | Vitamin B3 | about 5 mg to about 4000 mg |
| 112 | Vitamin B6 | about 1 mg to about 500 mg |
| 114 | Folic Acid | about 25 mg to about 20 mg |
| 116 | Quercetin | about 5 mg to about 1800 mg |
| 118 | Vitamin E | about 1 iu to about 800 iu |

Wine Headache Questionnaire

Name: _____

Date of birth: _____/_____/_____

Do you currently drink wine on a regular basis?     Yes / No
If yes, how many times a week?                _____
If yes, how many glasses on average per meal?     Yes / No
If yes, do you experience headaches?        Yes / No
What is the threshold, or how many glasses of wine do you drink, before experiencing headaches?   _____
How long have you experienced headaches from drinking wine?   _____
Are these headaches becoming worse over time?   Yes / No
Is the threshold for your wine induced headaches becoming lower over time?   Yes / No
What kind of wine do you prefer to drink? _____
Is there a particular kind of wine or grape varietal that triggers headaches more strongly than another? _____
How strong would you rate your typical wine headache (1-10)?  _____
How strong would you rate your most intense wine headache (1-10)?  _____
Are you sensitive to food additives?   Yes / No
Are you sensitive to colognes and perfumes?  Yes / No
Are you sensitive to medications?  Yes / No
Would being able to drink wine without headaches improve your quality of life?   Yes / No

NUTRITIONAL COMPOSITION FOR PROVIDING RELIEF FROM WINE INDUCED HEADACHES

CROSS-REFERENCE TO RELATED APPLICATIONS

This application claims the benefit of U.S. provisional application No. 62/160,538, filed May 12, 2015 and entitled NUTRITIONAL COMPOSITION FOR PROVIDING RELIEF FROM ALCOHOL-INDUCED HANGOVERS, which provisional application is incorporated by reference herein in its entirety.

FIELD OF THE INVENTION

The present invention relates generally to a nutritional composition that provides relief from headaches associated with minimal to moderate wine drinking. More so, the present invention relates to a nutritional composition which includes Molybdenum, Selenium, Vitamin B1, Vitamin B2, Vitamin B3, Vitamin B6, Folic acid, Quercetin, Vitamin E, and nitrogreens and provides relief for headaches from light to moderate consumption of wine. Clinical trials have also shown that the composition provides relief for sensitivities to aldehydes, sulfites, and phenols.

BRIEF DESCRIPTION OF THE DRAWINGS

The invention will now be described, by way of example, with reference to the accompanying drawings, in which:

FIG. 1 illustrates a table of typical ingredients for an exemplary nutritional composition for providing relief from wine induced headaches, in accordance with an embodiment of the present invention;

FIG. 3 illustrates a typical survey questionnaire for experimental subjects in administration of the nutritional composition, in accordance with an embodiment of the present invention.

Like reference numerals refer to like parts throughout the various views of the drawings.

DETAILED DESCRIPTION OF THE INVENTION

Figure 2:
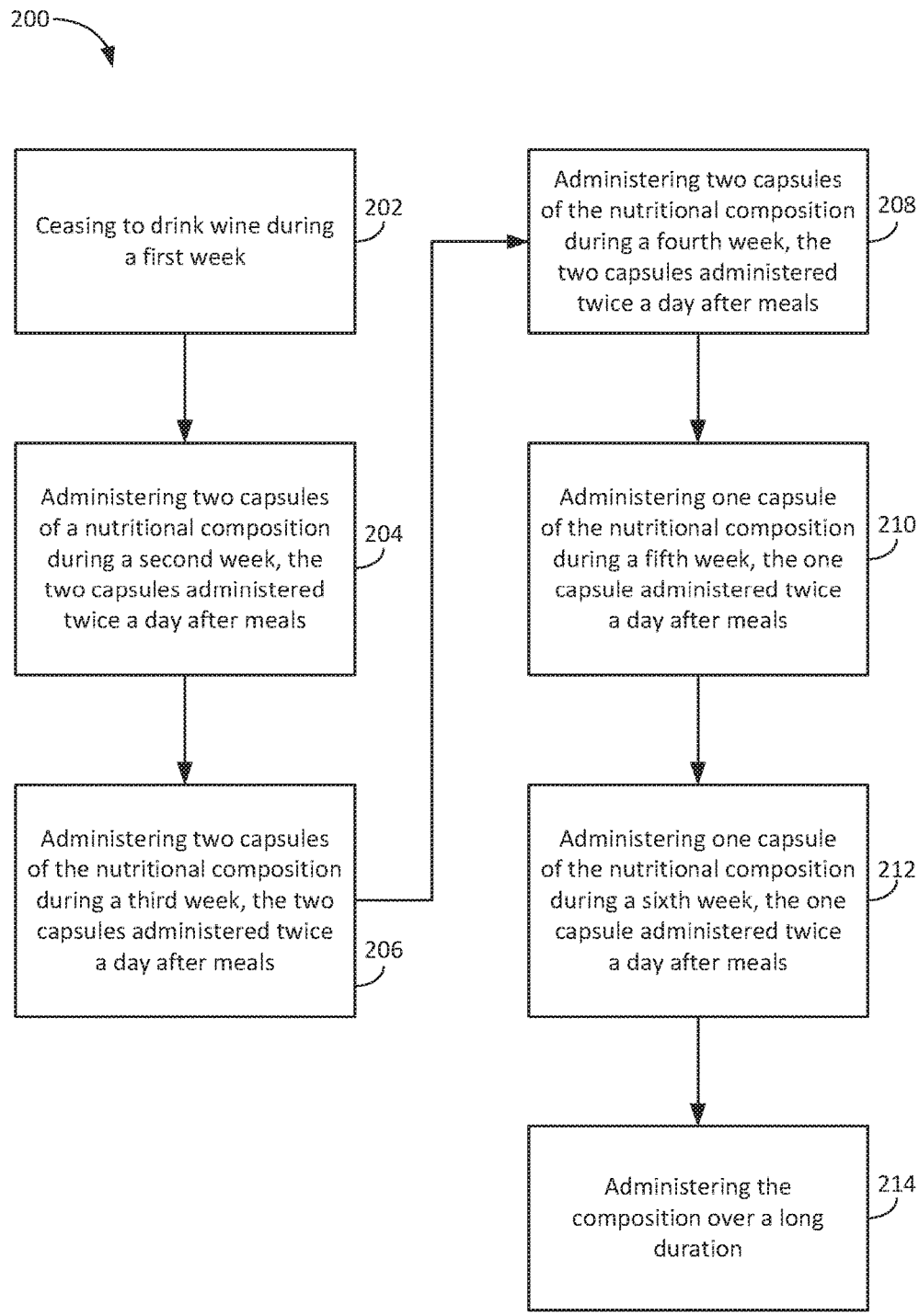
FIG. 2 illustrates a flowchart diagram of an exemplary method for use of a nutritional composition for providing relief from wine induced headaches, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in the FIGS. 1-3. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

An illustrative embodiment of a nutritional composition 100 to provide relief from headaches associated with minimal to moderate wine drinking is referenced in FIG. 1. The nutritional composition 100, hereinafter "composition 100", may include a dietary nutritional supplement that provides relief for light to moderate wine consumers who experience headaches triggered by light to moderate wine consumption. The present invention includes quantitative and qualitative aspects of the various ingredients of the composition 100, methods of preparing the composition 100 and methods of administering the composition 100, including experimental results and conclusions therefrom.

Those skilled in the art will recognize that a wine induced headache, and more specifically, a wine induced headache that results from light to moderate consumption of wine, causes an experience of various unpleasant physiological and psychological effects which can last for more than 24 hours. The symptoms of wine induced headache are known to occur within 15 minutes of wine consumption and may include headache, nausea and flushing.

Those skilled in the art, in light of the present teachings, will further understand that the biochemical processes involved in metabolizing wine constituents may contribute to wine induced headaches. Multiple causes of wine induced headaches have been proposed and include sensitivity to sulfites, phenols, aldehydes and tyramines mediated through liver metabolism, as well as histamines and prostaglandins mediated through systemic cellular biochemistry. The simplest and most familiar explanation for the cause of wine headaches is sensitivity to sulfites. Although research results have questioned it as being the sole cause for wine induced headaches, sulfite sensitivity is most likely one of its causes. Other causes for wine induced headaches that have been proposed and appear to bear weight from the scientific literature include sensitivities to histamines, phenols (tannins), prostaglandins, tyramines, and aldehydes.

Referring initially to FIG. 1 of the drawings, the composition 100 may include a pharmaceutically effective quantity of each of multiple ingredients to ameliorate headaches caused by light to moderate wine consumption. These ingredients may include Molybdenum 102, Selenium 104, Vitamin B1 106, Vitamin B2 108, Vitamin B3 110, Vitamin B6 112, Folic acid 114, Quercetin 116 and Vitamin E 118. In some alternative embodiments, the composition 100 may include nitrogreens. Nitrogreens include a proprietary blend of raw organic plant juices including raw organic grass juices (barley, wheat, oat, alfalfa, kamut), raw organic vegetable sprout concentrations (broccoli, cauliflower, kale), raw organic vegetable juices (beet, carrot), organic acerola extract and organic peppermint leaf. In some embodiments, the nitrogreens may be present in the composition 100 in a quantity of about 10 mg per capsule.

Predetermined quantities of the ingredients 102-118 may be mixed to form a composition mixture. Various ranges for the quantities of ingredients 102-118 may be used to form the composition mixture, depending on variables such as the body weight/fat of the subject, the amount of wine consumed and the type of wine consumed. Furthermore, the ingredients in the composition 100 are listed as Generally Recognized As Safe (GRAS). In some embodiments, the ingredients 102-118 may be mixed using standard laboratory procedures and equipment known in the art, including, without limitation, weighing, mixing, crushing, titrating, heating, cooling, and distilling. The composition 100 may be fabricated as a pill, a liquid, or a powder for administration. In some embodiments, the ingredients 102-118 for the composition 100 may form a synergistic combination with each other to enhance metabolism of wine constituents. Prescribed use of the composition 100 enhances the functionality of liver sulfation enzymes. Specifically, the composition 100 provides nutrient cofactor support which is essential to the functionality of the liver sulfation enzymes. Those skilled in the art will recognize that the liver sulfation enzymes perform metabolism (chemical transformations) of constituents that occur in wine. Although every biological tissue has some ability to metabolize drugs, the liver is the principal organ of drug metabolism because liver cells have extensive smooth endoplasmic reticulum. The liver is relatively large, has very high concentrations of drug-metabolizing enzyme systems relative to other organs and is the first organ perfused by chemicals absorbed in the gut.

The results of wine consumption surveys and trial uses of the composition 100 indicate that the composition 100 may be effective in improving tolerance of subjects to volatile environmental agents and food additives such as those found in alcohol, and specifically, wine. The composition 100 may include Molybdenum 102. In some embodiments, the optimal form of the Molybdenum 102 in the composition 100 may include a vegetable culture or organic salts of Molybdenum 102. The organic salt form of Molybdenum 102 may include, without limitation: glycinate; aspartate; gluconate; orotic acid; amino acid chelate; and mixtures thereof. The effective quantity of molybdenum 102 in a typical dose of the composition 100 may fall between about 10 mcg and about 600 mcg, with a preferred range of from about 50 mcg to about 400 mcg, and most optimally, a range of from about 100 mcg to about 200 mcg.

The composition 100 may include Selenium 104. In some embodiments, the optimal form of the Selenium 104 in the composition 100 may include a vegetable culture or organic salts of Selenium 104. The organic salt form of Selenium 104 may include, without limitation: methionine; aspartatic acid; orotic acid; amino acids; or inorganic forms such as sodium selenite, or mixtures thereof. The effective quantity of Selenium 104 in a typical dose of the composition 100 may fall between about 10 mcg and about 600 mcg, with a preferred range of from about 25 mcg to about 400 mcg and an optimal range of from about 50 mcg to about 100 mcg.

The composition 100 may include Vitamin B1 106. In some embodiments, the optimal form of the Vitamin B1 106 in the composition 100 may include the co-enzymatic active form co-carboxylase; thiamin diphosphate, thiamine monophosphate; thiamine triphosphate; salts of thiamine mononitrate or hydrochloride; or mixtures thereof. The effective quantity of Vitamin B1 106 in the composition 100 may fall between about 0.1 mg and about 2000 mg, with a preferred range of from about 0.5 mg to about 200 mg and an optimal range of from about 1 mg to about 10 mg.

The composition 100 may include Vitamin B2 108 (Riboflavin). Specifically, the composition 100 may include riboflavin-5-phosphate, which is the phosphorylated form of riboflavin. Those skilled in the art will recognize that riboflavin-5-phosphate is the activated form used in metabolic processes at the cellular level. It is significant to note that non-phosphorylated riboflavin must be phosphorylated in the liver before it can be utilized at the cellular level. Further, a user of the composition 100 may have genetic polymorphisms that prevent effective metabolism for phosphorylation of riboflavin. Use of riboflavin-5-phosphate overcomes this limitation and provides more consistent results. The effective quantity of Vitamin B2 108 in the composition 100 may fall between about 0.1 mg and about 400 mg, with a preferred range of from about 0.5 mg to about 25 mg and an optimal range of from about 1 mg to about 5 mg.

The composition 100 may include Vitamin B3 110 (Niacinamide). In some embodiments, the optimal form of the Vitamin B3 110 in the composition 100 may include niacinamde, niacin or mixtures thereof. The effective amount of Vitamin B3 110 in the composition 100 may fall between about 5 mg and about 4000 mg, with a preferred range of from about 10 mg to about 500 mg and an optimal range of from about 10 mg to about 100 mg.

The composition 100 may include Vitamin B6 112 (Pyridoxine). In some embodiments, the source for Vitamin B6 112 may include pyridoxine hydrochloride, a non-phosphorylated form. In some embodiments, the composition 100 may include pyridoxyl-5-phosphate, the phosphorylated form. In some embodiments, the composition 100 may include both the non-phosphorylated form and the phosphorylated form. In some embodiments, the optimal form for the Vitamin B6 112 in the composition 100 may include the co-enzymatic active form of pyridoxal 5 phosphate, the hydrochloride salt, pyridoxine HCl, or mixtures thereof. The effective quantity of Vitamin B6 112 in the composition 100 may fall between about 1 mg and about 500 mg, with a preferred range of from about 2 mg to about 200 mg and an optimal range of from about 5 mg to about 50 mg.

The composition 100 may include Folic acid 114. In some embodiments, the optimal form of the Folic acid 114 in the composition 100 may include a bioactive form such as (6S) 5 methyl-tetra-hydro-folic acid, Folic acid salts, folinic acid, folinic acid salts such as calcium folinate, or mixtures thereof. It is significant to note that a very large percentage of the population has the genetic polymorphism that down-regulates the conversion of Folic acid 114 to methylfolate. Inclusion of optimal forms of Folic acid 114, when included in the composition 100, may overcome limits in folic acid metabolism related to this down-regulation. The effective quantity of Folic acid 114 in the composition 100 may fall between about 25 mcg and about 20 mg, with a preferred range of from about 0 mcg to about 800 mcg and an optimal range of from about 100 mcg to about 600 mcg.

The composition 100 may include Quercetin 116. In some embodiments, the optimal form of the Quercetin 116 may include Quercetin di-hydrate and anhydrous Quercetin. Other possible forms of Quercetin 116 used in the composition 100 may include micro-ionized powders of Quercetin 116, liposomal preparations of Quercetin 116, or mixtures thereof. The effective quantity of Quercetin 116 in the composition 100 may fall between about 5 mg and about 1800 mg, with a preferred range of from about 20 mg to about 200 mg, and an optimal range of from about 50 mg to about 100 mg. The composition 100 may include Vitamin E 118. Vitamin E 118 belongs to a group of compounds including both tocopherols and tocotrienols. Vitamin E 118 has many biological functions, the antioxidant function being the most important and best known. Other functions of Vitamin E 118 include enzymatic activities, gene expression, and neurological function(s). One of the most important functions of Vitamin E is cell signaling. For the present composition 100, the optimal effectiveness of Vitamin E 118 is in an emulsified form. The effective quantity of Vitamin E 118 in the composition 100 may fall between about 1 IU and about 800 IU, with a preferred range of from about 10 IU to about 400 IU, and an optimal range of from about 45 IU to about 55 IU.

In some embodiments, the composition 100 may include a sulfur-rich cruciferous vegetable culture included as a synergistic component supporting liver sulfation enzymes.

Controversy exists over the precise mechanism(s) which cause wine headaches, especially red wine headaches. Proposed mechanisms include sensitivity to vectors such as sulfites, phenols/tannins, mold/yeast, histamines and tyramines, or a combination of these. Interestingly, sensitivity reactions to these components are mediated in the liver, where the metabolic benefits provided by the composition 100 occur. As discussed below, the ingredients of the composition 100 address all of these mechanisms.

One possible cause of wine induced headaches is prostaglandins. Consumption of wine results in overproduction of prostaglandins in the prostaglandin 2 family (PG2). This overproduction of prostaglandins may explain why some wine drinkers experience relief by using NSAIDs such as aspirin. Upregulation of prostaglandins in the prostaglandin 1 and 3 families (PG1 and PG3) down regulates the pro-inflammatory effects of the PG2. Though diet certainly influences these prostaglandins, Delta-6-saturase is a critical enzyme in the conversion of the omega-6 fatty acids to the anti-inflammatory PG1s and the omega-3 fatty acids to the anti-inflammatory PG3s. Delta-6-saturase production is upregulated by the nutrients Vitamin B6 112, Magnesium, Zinc, and niacin, or Vitamin B3 110.

Another possible cause of wine induced headaches is histamine. Histamine is metabolized by the nutrients Folic acid 114, Quercetin 116, Vitamin B6 112, and betaine.

Yet another possible cause of wine induced headaches is tyramine. Tyramine is broken down by monoamine oxidase (MAO), both MAO-A and MAO-B. Nutrient cofactors for metabolism of MAO include riboflavin, or Vitamin B2 108, and Fe.

Yet another possible cause of wine induced headaches is sulfite. Sulfite oxidase (SO) is the enzyme that converts sulfite to SO. Production of SO requires the ingredients Molybdenum 102 and riboflavin, or Vitamin B2 108. Sulfation in general is supported by the nutrients Vitamin B1 106, Folic acid 114, Magnesium, Vitamin B6 112, and methyl donors such as choline and Vitamin B15.

Yet another possible cause of wine induced headaches is Phenol/Tannin. Phenol-sulfotransferase (PST) is the enzyme that sulfates phenols including tannins. Those skilled in the art will recognize that phenols have hormetic effects that are biologically beneficial. But the sulfation of phenols lowers the inherent toxicity associated with them and allows excretion of phenols via the kidneys. Deficiency of dietary sulfur, though not directly a cofactor for the production of PST, is required for the sulfation process. Additionally, red wine has been shown to contain a potent inhibitor of phenol-sulphotransferase (PST). PST is also an enzyme that metabolizes monoamines such as tyramine. Activity of PST is down-regulated by excessive Vitamin B6 112 and is up-regulated by many vegetables. One of the most potent inducers of higher PST levels is broccoli, one of the plant extracts found in nitrogreens.

Yet another possible cause of wine induced headaches includes mold/yeast and aldehydes Molds and yeasts are known to produce acetaldehydes, and much of the sensitivity to yeast/mold exposures are likely due to acetaldehyde loads. Actetaldehyde, a toxin generally and a neurotoxin specifically, is metabolized to acetic acid through acetylation with the cofactor nutrients Molybedenum 102, iron, niacinamide or Vitamin B3 110, and riboflavin or Vitamin B2 108. It is significant to note that allergic reactions may be mediated by mold or yeast proteins, but treating these allergic reactions may be outside the scope of the composition 100.

General aldehyde sensitivity is a very likely cause of wine headaches. Individuals with general aldehyde sensitivity are typically also sensitive to perfumes, smoke, and volatile chemicals. Breakdown of aldehydes via aldehyde dehydrogenase is supported with Zinc, Molybdenum 102, Selenium 104, niacinamide or Vitamin B3 110, riboflavin or Vitamin B2 108, iron, and Vitamin E 118.

As illustrated in FIG. 2, a method 200 for use of the composition 100 (FIG. 1) is illustrated. The method 200 was derived through trial and error and required six sequential weeks of administering the composition 100 to subjects in capsule form and in predetermined quantities with predetermined amounts of wine.

The method 200 may include an initial Step 202 of a subject's ceasing to drink wine during a first week. At the time he or she stops drinking wine, the subject may take two capsules of the composition 100 twice a day after meals and may refrain from consuming wine thereafter. In one study, it was found that no headaches were reported by the subject after the capsules were administered.

A Step 204 of the method 200 may include administering two capsules of the composition 100 to the subject during a second week, twice a day after meals. In some embodiments, the subject may consume 3 ounces of wine with a meal three times on nonconsecutive days during the second week. In one study which included 13 subjects, during the second week, 3 ounces of trial wine were consumed over 3 nonconsecutive days, and 2 capsules were administered twice a day after meals, 5 subjects reported headaches.

In some embodiments, a Step 206 of the method 200 may include administering two capsules of the composition 100 to a subject twice a day after meals during a third week.

In some embodiments, the subject may consume 6 ounces of trial wine with a meal three times on nonconsecutive days during the third week.

In one study which included 13 subjects, during the third week, three 6 ounce glasses of trial wine were consumed during a three nonconsecutive and 2 capsules of the composition 100 were administered to the subjects twice day after meals. In one exemplary experiment, 3 subjects reported headaches.

In some embodiments, a Step 208 of the method 200 may include administering two capsules of the composition 100 to a subject during a fourth week, twice a day after meals. In one study which included 13 subjects, during the fourth week, 6 ounces of wine was consumed during a meal twice on nonconsecutive days, and 12 ounces of wine were consumed with a meal on a third nonconsecutive day. Two capsules of the composition 100 were administered to the subjects twice a day after meals during this week. In the study, 2 subjects reported headaches.

In some embodiments, a Step 210 of the method 200 may include administering one capsule of the composition 100 to a subject during a fifth week, twice a day after meals, with 6 ounces of a trial wine consumed after a meal on nonconsecutive days. In one study which included 13 subjects, during the fifth week, 6 ounces of trial wine were consumed during a meal on three nonconsecutive days and 1 capsule of the composition 100 was administered to the subject twice a day after meals. In the study, 2 subjects reported headaches.

In some embodiments, a Step 212 of the method 200 may include administering one capsule of the composition 100 to a subject during a sixth week, twice a day after meals, with 6 ounces of a trial wine consumed after a meal twice this week on nonconsecutive days. The subject drinks 12 ounces of wine with a meal once at the end of the sixth week and non-consecutively to other days of drinking wine. In one study which included 13 subjects, during the sixth week, the subject consumed 6 ounces of wine after a meal on two nonconsecutive days and two 6 ounce glasses of wine with a third meal at the end of the third week and non-consecutively to other days drinking wine with 1 subject reporting headaches.

In some embodiments, a final Step 214 of the method 200 may include administering one or two capsules of the composition 100 to a subject over a long period of time. This treatment regimen may be required in cases of genetic predisposition to wine headaches, and the nutritional support imparted by the composition 100 may upregulate some low functioning enzyme systems, primarily for liver sulfation. Step 214 may be implemented as part of a long term solution that may be administered to a subject throughout the subject's lifetime. Checkups with a medical professional may be required in the event that the subject experiences side effects. The increased wine tolerance may result from increased metabolism of wine components, resulting in nutritional upregulation of the enzyme systems involved in the metabolic pathways over time.

The composition 100 was studied with multiple test subjects over a period of weeks. A wine headache questionnaire 300 was given to the test subjects at the beginning of the trial. After the subjects were given the questionnaire 300, predetermined quantities of wine were administered to the subjects. As shown in FIG. 3, subjects for the questionnaire 300 were wine drinkers who in the past had consistently experienced wine headaches after drinking one glass of wine (six ounces or less). Typical inquiries on the questionnaire 300 may include, without limitation, personal identification information; drinking history; past effects of alcohol usage; sensitivities to different wine constituents; and drinking thresholds of the subject.

In one exemplary experiment, the resolution for wine induced headaches at the end of the study was 85%. Ultimately, subjects may titrate the optimal dosage based upon relief from headaches while drinking wine. It is significant to note that that many of the experimental subjects reported significant improvements in tolerance to phenols and aldehydes. The link for a video testimonial from one of the subjects is: https://vimeo.com/111049544.

In one possible embodiment that explains the improved reaction to wine after use of the composition 100, improved sulfation of phenolic compounds may be a cause of the ameliorating effects of the composition 100. Those skilled in the art will recognize that sensitivity to phenolics is common, and exposure to phenolics is widely distributed. Phenols have been strongly attributed to headaches and are known to be a major component of food dyes, artificial flavors, preservatives, flavonoids, carotenoids, and salicylates. It is also interesting to note is that red grapes are high in salicylates.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for using a nutritional composition for providing relief from wine-induced headaches associated with minimal to moderate wine drinking, the method comprising:

ceasing to drink wine for a selected period of time; and administering a composition including a composition mixture, in the form of a capsule or tablet, having a pharmaceutically effective quantity of each of the following ingredients to ameliorate headaches caused by wine consumption wherein a cause of wine-induced headaches is sensitivity to a constituent in the wine selected from the group consisting of sulfites, histamines, phenols, prostaglandins, tyramines, and aldehydes, the composition comprising:

from about 10 mcg to about 600 mcg Molybdenum;
from about 10 mcg to about 600 mcg Selenium;
from about 0.1 mg to about 2000 mg Vitamin B1;
from about 0.01 mg to 400 mg Vitamin B2;
from about 5 mg to about 4000 mg Vitamin B3;
from about 1 mg to about 500 mg Vitamin B6;
from about 25 mcg to about 20 mg Folic acid;
from about 5 mg to about 1800 mg Quercetin; and
from about 1 IU to about 800 IU Vitamin E wherein:
ceasing to drink wine for a selected period of time comprises ceasing to drink wine during a first week; and administering a composition including a composition mixture having a pharmaceutically effective quantity of each of the following ingredients to ameliorate headaches caused by wine consumption comprises: administering two capsules of a nutritional composition during a second week, the two capsules administered twice a day after meals; administering two capsules of the nutritional composition during a third week, the two capsules administered twice a day after meals; administering two capsules of the nutritional composition during a fourth week, the two capsules administered twice a day after meals; administering one capsule of the nutritional composition during a fifth week, the one capsule administered twice a day after meals; and administering one capsule of the nutritional composition during a sixth week, the one capsule administered twice a day after meals.

2. The method of claim 1 wherein administering the composition comprises administering the composition mixture in which the Molybdenum is present in the composition mixture in a quantity of from about 100 mcg to about 200 mcg, the Selenium is present in the composition mixture in a quantity of from about 50 mcg to about 100 mcg, the Vitamin B1 is present in the composition mixture in a quantity of from about 1 mg to about 10 mg, the Vitamin B2 is present in the composition mixture in a quantity of from about 1 mg to about 5 mg, the Vitamin B3 is present in the composition mixture in a quantity of from about 10 mg to about 100 mg, the Vitamin B6 is present in the composition mixture in a quantity of from about 5 mg to about 50 mg, the Folic acid is present in the composition mixture in a quantity of from about 100 mcg to about 600 mcg, the Quercetin is present in the composition mixture in a quantity of from about 50 mg to about 100 mg and the Vitamin E is present in the composition mixture in a quantity of from about 45 IU to about 55 IU.

3. The method of claim 1 wherein administering the composition comprises administering the composition mixture including nitrogreen.

\* \* \* \* \*